United States Patent
Ito et al.

(10) Patent No.: US 6,541,236 B2
(45) Date of Patent: Apr. 1, 2003

(54) PROTEIN HAVING GLUTAMINASE ACTIVITY AND GENE ENCODING THE SAME

(75) Inventors: Kotaro Ito, Noda (JP); Genryou Umitsuki, Noda (JP); Yasuji Koyama, Noda (JP)

(73) Assignee: Kikkoman Corporation, Chiba-ken (JP)

( * ) Notice: Subject to any disclaimer, the term of this patent is extended or adjusted under 35 U.S.C. 154(b) by 0 days.

(21) Appl. No.: 09/946,678

(22) Filed: Sep. 6, 2001

(65) Prior Publication Data

US 2002/0106782 A1 Aug. 8, 2002

(30) Foreign Application Priority Data

Sep. 6, 2000 (JP) ........................................ 2000-270371

(51) Int. Cl.[7] ............................ C12N 9/78; C12N 15/00; C12N 1/20; C07H 21/04
(52) U.S. Cl. ................. 435/227; 435/320.1; 435/223.2; 435/440; 435/6; 435/252.3; 536/23.2
(58) Field of Search ............................ 435/227, 320.1, 435/257.3, 232.2, 440, 6, 272.2; 536/23.2

(56) References Cited

U.S. PATENT DOCUMENTS 6,063,409 A    5/2000  Sato et al. .................... 426/52

FOREIGN PATENT DOCUMENTS

JP    A11332553    12/1999

OTHER PUBLICATIONS

Huser et al. Cloning, sequence analysis, and expression of ansB from *Pseudomonas fluorescens*, encoding periplasmic glutaminase/asparaginase. FEMS Microbiol Lett. 15;178 (2);327–335. Sep. 1999.*

* cited by examiner

*Primary Examiner*—Ponnathapu Achutamurthy
*Assistant Examiner*—Yong Pak
(74) *Attorney, Agent, or Firm*—Birch, Stewart, Kolasch & Birch, LLP

(57) ABSTRACT

There are disclosed a protein having an amino acid sequence represented by amino acid numbers 1 to 684 or 49 to 684 shown in SEQ ID NO:2, or a protein having a glutaminase activity in which one or more amino acids is/are deleted from, substituted by, inserted to or added to the amino acid sequence of the above protein; a gene containing DNA encoding the above protein or a gene encoding a protein which hybridizes with the DNA of the above gene under a stringent condition and has a glutaminase activity; a recombinant DNA containing the above gene; a transformant or a transductant containing the above recombinant DNA; and a process for producing glutaminase which comprises culturing the above transformant or the above transductant and collecting glutaminase from a culture medium.

12 Claims, No Drawings

SEQUENCE LISTING

<160> NUMBER OF SEQ ID NOS: 27

<210> SEQ ID NO 1
<211> LENGTH: 2055
<212> TYPE: DNA
<213> ORGANISM: Cryptococcus nodaensis

<400> SEQUENCE: 1

| | | | | | |
|---|---|---|---|---|---|
| atggccacaa | gcatcaacat | gctggccctc | ctgtacggtc | tgttgagtgc | ttcgcccgct | 60 |
| ttgtctgcgc | agcttgccgg | caatgaggac | tacgcccacg | ccgcaaggca | atcgctcgct | 120 |
| cacaatccca | cattcggcaa | acgcggcgtg | accagcggtc | tcgcatttca | gccggcttcc | 180 |
| gtctccttca | ccgtgggcga | caagcagtat | ttgtccccca | ccggagccca | gttcaggcgg | 240 |
| tacagcatcg | gagctgaatg | gggattggac | gccctcgctg | acaaagctt | ggcggttacc | 300 |
| gttctcgaag | tggagggcga | ggtcacctgc | gatgttctgg | ggagcaagct | ggacaagttc | 360 |
| caacaggcgg | acgatgtctg | ggacacgtca | ttcctcaacg | gcatcttcct | gacgactacg | 420 |
| tcgtcttacc | acgtagcaag | cgatgtttct | agctgtttgg | aaggctgggg | aggatctctg | 480 |

-continued

```
gttgtgaaga gtgggaatgc tacgtccgac gtggagggtg tgagcgttgc caaagtcgcg    540
agcgtatcga ttccacaagg cccgtatctc gcccacgtca acgtaacat cacactcacg     600 caaatctatc gatcgtaccg cgacgaagca caggccttca ccgccggcgt cattcacact    660
gaagacaaca ccttcgtcga tctctccacc cccgtccctg cgctcaacac cctctctatc    720
tctgtcccgt cacgacttta cactcaac gtgcctaatc caagacccct ggaagggagg     780
cgaatcgctg tcaaggactt gttcgacatg gccggactga agactggagg aggtaacagg    840
gcatactaca acacgtatcc cgccaagaat gttaccgcga tcgccataca gcgattggtt    900
gatcaaggtg gcatcatcgt tggccgggtc aagacgagcc aatttgccaa cggagaggat    960
gccacggcgg actgggtgga ccagatgtgc cccttcaacc cgcgagggga tggatatcag   1020
cagccggcgt cgtcctcaag cggtccgggt gcggccgcag gtgcatacga ctggctcgac   1080
catacgatcg gatccgatac cggtggtagc atcatcgatc cggcctcggt acaagggta    1140 tatggccttc gcccctcatg gagtgctatt ccctcgagg gcgcaatccc tcttcaggcc    1200
acccaagaca cagcagggtt cttcgcgcga cgctcaat ccgggctcgc gttcgcccag    1260
ggatggtatg gtgaccgttt cggcaacttt tcaaccctgc ccaccaatct catcttgccg    1320
aacagctcgt gggagtttgc ccccgacttt gccggcgcgg agcagttcaa cgccttccgt   1380
gacggccttc ttgaccttgt caagccggct tcagtcgacg tgcgagactt tgagggctat   1440
tggaacacgt caggccgttt cgaacaggtc aatgccaccg cttccgatta cctatacgag    1500
gtctacgcca acctgatcac ctactaccaa tggaacaact ttggcaaact ctggtacgaa    1560
gattacgccg agcagaacga tggacgccaa ccttttgtgg acccgtcgcc tttggtccga    1620
tggacctacg cacgggacaa cctaactgag gctgacttca actcgtcgac cgccaaaaag   1680
gagctcttca aggagttcat cgacaccgag gtgttggtca aggacaactc gacgtgctcg    1740
agcgccatct acgtggcgcc gtatggcctg gctcagactg cctaccgtaa catctataag    1800
caagctgcga gcgttccgtt cggcttctac tatcccgcgc agttctctgg ggtgcctcag    1860
ctgatcgtcc ccatcggcca gctaccatac gagtcaacca tcacgaacca taccgagtac    1920
ctgcccctga ctgtgacgct gtacgccgcc gccgactgcg attacgtcct gtgggatctg    1980
gctgcaaagt tggaggcggc tggagtgacg agctcggttg ctgcgggtgc agtcgcctac    2040
ccagatcgcg tgtag                                                   2055
```

<210> SEQ ID NO 2
<211> LENGTH: 684
<212> TYPE: PRT
<213> ORGANISM: Cryptococcus nodaensis

<400> SEQUENCE: 2

```
Met Ala Thr Ser Ile Asn Met Leu Ala Leu Leu Tyr Gly Leu Leu Ser
 1               5                  10                  15

Ala Ser Pro Ala Leu Ser Ala His Val Ala Gly Asn Glu Asp Tyr Ala
             20                  25                  30

His Ala Ala Arg Gln Ser Leu Ala His Asn Pro Thr Phe Gly Lys Arg
         35                  40                  45

Gly Val Thr Ser Gly Leu Ala Phe Gln Pro Ala Ser Val Ser Phe Thr
     50                  55                  60

Val Gly Asp Lys Gln Tyr Leu Ser Pro Thr Gly Ala Gln Phe Arg Arg
 65                  70                  75                  80

Tyr Ser Ile Gly Ala Glu Trp Gly Leu Asp Ala Leu Ala Gly Gln Ser
```

-continued

```
                85                  90                  95
Leu Ala Val Thr Val Leu Glu Val Glu Gly Glu Val Thr Cys Asp Val
                100                 105                 110
Leu Gly Ser Lys Leu Asp Lys Phe Gln Gln Ala Asp Asp Val Trp Asp
                115                 120                 125
Thr Ser Phe Leu Asn Gly Ile Phe Leu Thr Thr Thr Ser Ser Tyr His
                130                 135                 140
Val Ala Ser Asp Val Ser Ser Cys Leu Glu Gly Trp Gly Gly Ser Leu
145                 150                 155                 160
Val Val Lys Ser Gly Asn Ala Thr Ser Asp Val Glu Gly Val Ser Val
                165                 170                 175
Ala Lys Val Ala Ser Val Ser Ile Pro Gln Gly Pro Tyr Leu Ala His
                180                 185                 190
Val Asn Gly Asn Ile Thr Leu Thr Gln Ile Tyr Arg Ser Tyr Arg Asp
                195                 200                 205
Glu Ala Gln Ala Phe Thr Ala Gly Val Ile His Thr Glu Asp Asn Thr
                210                 215                 220
Phe Val Asp Leu Ser Thr Pro Val Pro Ala Leu Asn Thr Leu Ser Ile
225                 230                 235                 240
Ser Val Pro Ser Arg Leu Tyr Thr Leu Asn Val Pro Asn Pro Arg Pro
                245                 250                 255
Leu Glu Gly Arg Arg Ile Ala Val Lys Asp Leu Phe Asp Met Ala Gly
                260                 265                 270
Leu Lys Thr Gly Gly Asn Arg Ala Tyr Tyr Asn Thr Tyr Pro Ala
                275                 280                 285
Lys Asn Val Thr Ala Ile Ala Ile Gln Arg Leu Val Asp Gln Gly Gly
                290                 295                 300
Ile Ile Val Gly Arg Val Lys Thr Ser Gln Phe Ala Asn Gly Glu Asp
305                 310                 315                 320
Ala Thr Ala Asp Trp Val Asp Gln Met Cys Pro Phe Asn Pro Arg Gly
                325                 330                 335
Asp Gly Tyr Gln Gln Pro Ala Ser Ser Ser Gly Pro Gly Ala Ala
                340                 345                 350
Ala Gly Ala Tyr Asp Trp Leu Asp His Thr Ile Gly Ser Asp Thr Gly
                355                 360                 365
Gly Ser Ile Ile Asp Pro Ala Ala Ser Val Gln Gly Val Tyr Gly Leu
370                 375                 380
Arg Pro Ser Trp Ser Ala Ile Ser Leu Glu Gly Ala Ile Pro Leu Gln
385                 390                 395                 400
Thr Gln Asp Thr Ala Gly Phe Phe Ala Arg Asp Ala Gln Ser Gly Leu
                405                 410                 415
Ala Phe Ala Gln Gly Trp Tyr Gly Asp Arg Phe Gly Asn Phe Ser Thr
                420                 425                 430
Leu Pro Thr Asn Leu Ile Leu Pro Asn Ser Ser Trp Glu Phe Ala Pro
                435                 440                 445
Asp Phe Ala Gly Ala Glu Gln Phe Asn Ala Phe Arg Asp Gly Leu Leu
                450                 455                 460
Asp Leu Val Lys Pro Ala Ser Val Asp Val Arg Asp Phe Glu Gly Tyr
465                 470                 475                 480
Trp Asn Thr Ser Gly Arg Phe Glu Gln Val Asn Ala Thr Ala Ser Asp
                485                 490                 495
Tyr Leu Tyr Glu Val Tyr Ala Asn Leu Ile Thr Tyr Tyr Gln Trp Asn
                500                 505                 510
```

```
Asn Phe Gly Lys Leu Trp Tyr Glu Asp Tyr Ala Glu Gln Asn Asp Gly
            515                 520                 525

Arg Gln Pro Phe Val Asp Pro Ser Pro Leu Val Arg Trp Thr Tyr Ala
        530                 535                 540

Arg Asp Asn Leu Thr Glu Ala Asp Phe Asn Ser Ser Thr Ala Lys Lys
545                 550                 555                 560

Glu Leu Phe Lys Glu Phe Ile Asp Thr Glu Val Leu Val Lys Asp Asn
                565                 570                 575

Ser Thr Cys Ser Ser Ala Ile Tyr Val Ala Pro Tyr Gly Leu Ala Gln
            580                 585                 590

Thr Ala Tyr Arg Asn Ile Tyr Lys Gln Ala Ala Ser Val Pro Phe Gly
            595                 600                 605

Phe Tyr Tyr Pro Ala Gln Phe Ser Gly Val Pro Gln Leu Ile Val Pro
        610                 615                 620

Ile Gly Gln Leu Pro Tyr Glu Ser Thr Ile Thr Asn His Thr Glu Tyr
625                 630                 635                 640

Leu Pro Leu Thr Val Thr Leu Tyr Ala Ala Asp Cys Asp Tyr Val
                645                 650                 655

Leu Trp Asp Leu Ala Ala Lys Leu Glu Ala Ala Gly Val Thr Ser Ser
            660                 665                 670

Val Ala Ala Gly Ala Val Ala Tyr Pro Asp Arg Val
            675                 680

<210> SEQ ID NO 3
<211> LENGTH: 20
<212> TYPE: PRT
<213> ORGANISM: Cryptococcus nodaensis

<400> SEQUENCE: 3

Gly Val Thr Ser Gly Leu Ala Phe Gln Pro Ala Ser Val Ser Phe Thr
1               5                   10                  15

Val Gly Asp Lys
            20

<210> SEQ ID NO 4
<211> LENGTH: 16
<212> TYPE: PRT
<213> ORGANISM: Cryptococcus nodaensis

<400> SEQUENCE: 4

Lys Val Ala Ser Val Ser Ile Pro Gln Gly Pro Tyr Leu Ala His Val
1               5                   10                  15

<210> SEQ ID NO 5
<211> LENGTH: 13
<212> TYPE: PRT
<213> ORGANISM: Cryptococcus nodaensis

<400> SEQUENCE: 5

Ser Val Ser Ile Pro Gln Gly Pro Tyr Leu Ala His Val
1               5                   10

<210> SEQ ID NO 6
<211> LENGTH: 15
<212> TYPE: PRT
<213> ORGANISM: Cryptococcus nodaensis
<220> FEATURE:
<221> NAME/KEY: MISC_FEATURE
<222> LOCATION: (14)..(14)
<223> OTHER INFORMATION: Xaa = any amino acid, unknown, or other
```

<400> SEQUENCE: 6

Gly Val Thr Ser Gly Leu Ala Phe Gln Pro Ala Ser Val Xaa Phe
1               5                   10                  15

<210> SEQ ID NO 7
<211> LENGTH: 11
<212> TYPE: PRT
<213> ORGANISM: Cryptococcus nodaensis

<400> SEQUENCE: 7

Leu Trp Tyr Glu Asp Tyr Ala Glu Gln Asn Asp
1               5                   10

<210> SEQ ID NO 8
<211> LENGTH: 8
<212> TYPE: PRT
<213> ORGANISM: Cryptococcus nodaensis

<400> SEQUENCE: 8

Glu Phe Ile Asp Thr Glu Val Leu
1               5

<210> SEQ ID NO 9
<211> LENGTH: 5
<212> TYPE: PRT
<213> ORGANISM: Cryptococcus nodaensis
<220> FEATURE:
<221> NAME/KEY: MISC_FEATURE
<222> LOCATION: (1)..(1)
<223> OTHER INFORMATION: Xaa = any amino acid, unknown, or other

<400> SEQUENCE: 9

Xaa Ser Gln Phe Ala
1               5

<210> SEQ ID NO 10
<211> LENGTH: 29
<212> TYPE: DNA
<213> ORGANISM: Artificial Sequence
<220> FEATURE:
<223> OTHER INFORMATION: Primer Directed to Cryptococcus nodanesis
<221> NAME/KEY: misc_feature
<222> LOCATION: (1)..(29)
<223> OTHER INFORMATION: n = a, c, g, t, any, unknown, or other

<400> SEQUENCE: 10
ggngtnacnw snggnytngc nttycarcc                                        29

<210> SEQ ID NO 11
<211> LENGTH: 23
<212> TYPE: DNA
<213> ORGANISM: Artificial Sequence
<220> FEATURE:
<223> OTHER INFORMATION: Primer Directed to Cryptococcus nodanesis
<221> NAME/KEY: misc_feature
<222> LOCATION: (18)..(18)
<223> OTHER INFORMATION: n = a, c, g, t, any, unknown, or other

<400> SEQUENCE: 11
tggtaygarg aytaygcnga rca                                              23

<210> SEQ ID NO 12
<211> LENGTH: 23
<212> TYPE: DNA
<213> ORGANISM: Artificial Sequence
<220> FEATURE:

```
<223> OTHER INFORMATION: Primer Directed to Cryptococcus nodanesis
<221> NAME/KEY: misc_feature
<222> LOCATION: (9)..(9)
<223> OTHER INFORMATION: n = a, c, g, t, any, unknown, or other

<400> SEQUENCE: 12
ttytgytcng crtartcytc rta                                           23

<210> SEQ ID NO 13
<211> LENGTH: 23
<212> TYPE: DNA
<213> ORGANISM: Artificial Sequence
<220> FEATURE:
<223> OTHER INFORMATION: Primer Directed to Cryptococcus nodanesis
<221> NAME/KEY: misc_feature
<222> LOCATION: (1)..(23)
<223> OTHER INFORMATION: n = a, c, g, t, any, unknown, or other

<400> SEQUENCE: 13
arnacytcng trtcdatraa ytc                                           23

<210> SEQ ID NO 14
<211> LENGTH: 25
<212> TYPE: DNA
<213> ORGANISM: Artificial Sequence
<220> FEATURE:
<223> OTHER INFORMATION: Primer Directed to Cryptococcus nodanesis

<400> SEQUENCE: 14
caccgtgggc gacaagcagt atttg                                         25

<210> SEQ ID NO 15
<211> LENGTH: 25
<212> TYPE: DNA
<213> ORGANISM: Artificial Sequence
<220> FEATURE:
<223> OTHER INFORMATION: Primer Directed to Cryptococcus nodanesis

<400> SEQUENCE: 15
ccacgagctg ttcggcaaga tgaga                                         25

<210> SEQ ID NO 16
<211> LENGTH: 30
<212> TYPE: DNA
<213> ORGANISM: Artificial Sequence
<220> FEATURE:
<223> OTHER INFORMATION: Primer Directed to Cryptococcus nodanesis

<400> SEQUENCE: 16
atcgtatggt cgagccagtc gtatgcacct                                    30

<210> SEQ ID NO 17
<211> LENGTH: 30
<212> TYPE: DNA
<213> ORGANISM: Artificial Sequence
<220> FEATURE:
<223> OTHER INFORMATION: Primer Directed to Cryptococcus nodanesis

<400> SEQUENCE: 17
aggtctacgc caacctgatc acctactacc                                    30

<210> SEQ ID NO 18
<211> LENGTH: 30
<212> TYPE: DNA
<213> ORGANISM: Artificial Sequence
<220> FEATURE:
<223> OTHER INFORMATION: Primer Directed to Cryptococcus nodanesis
```

```
<400> SEQUENCE: 18
tccaatcccc attcagctcc gatgctgtac                                    30

<210> SEQ ID NO 19
<211> LENGTH: 30
<212> TYPE: DNA
<213> ORGANISM: Artificial Sequence
<220> FEATURE:
<223> OTHER INFORMATION: Primer Directed to Cryptococcus nodanesis

<400> SEQUENCE: 19
aaagtcgcga gcgtatcggt gagtgaggga                                    30

<210> SEQ ID NO 20
<211> LENGTH: 26
<212> TYPE: DNA
<213> ORGANISM: Artificial Sequence
<220> FEATURE:
<223> OTHER INFORMATION: Primer Directed to Cryptococcus nodanesis

<400> SEQUENCE: 20
catcctctcc gttggcaaat tggctc                                        26

<210> SEQ ID NO 21
<211> LENGTH: 25
<212> TYPE: DNA
<213> ORGANISM: Artificial Sequence
<220> FEATURE:
<223> OTHER INFORMATION: Primer Directed to Cryptococcus nodanesis

<400> SEQUENCE: 21
caccgtgggc gacaagcagt atttg                                         25

<210> SEQ ID NO 22
<211> LENGTH: 29
<212> TYPE: DNA
<213> ORGANISM: Artificial Sequence
<220> FEATURE:
<223> OTHER INFORMATION: Primer Directed to Cryptococcus nodanesis

<400> SEQUENCE: 22
caaaatggcc acaagcatca acatgctgg                                     29

<210> SEQ ID NO 23
<211> LENGTH: 25
<212> TYPE: DNA
<213> ORGANISM: Artificial Sequence
<220> FEATURE:
<223> OTHER INFORMATION: Primer Directed to Cryptococcus nodanesis

<400> SEQUENCE: 23
cagcgatgac ctatcgcgat tttgc                                         25

<210> SEQ ID NO 24
<211> LENGTH: 36
<212> TYPE: DNA
<213> ORGANISM: Artificial Sequence
<220> FEATURE:
<223> OTHER INFORMATION: Primer Directed to Cryptococcus nodanesis

<400> SEQUENCE: 24
gcaggtacca tggccacaag catcaacatg ctggcc                             36

<210> SEQ ID NO 25
```

-continued

```
<211> LENGTH: 36
<212> TYPE: DNA
<213> ORGANISM: Artificial Sequence
<220> FEATURE:
<223> OTHER INFORMATION: Primer Directed to Cryptococcus nodanesis

<400> SEQUENCE: 25
attgaattcc tacacgcgat ctgggtaggc gactgc                              36

<210> SEQ ID NO 26
<211> LENGTH: 29
<212> TYPE: DNA
<213> ORGANISM: Artificial Sequence
<220> FEATURE:
<223> OTHER INFORMATION: Primer Directed to Cryptococcus nodanesis

<400> SEQUENCE: 26
ggcgaattcg gcgtgaccag cggtctcgc                                     29

<210> SEQ ID NO 27
<211> LENGTH: 31
<212> TYPE: DNA
<213> ORGANISM: Artificial Sequence
<220> FEATURE:
<223> OTHER INFORMATION: Primer Directed to Cryptococcus nodanesis

<400> SEQUENCE: 27
ttgccgcggc tacacgcgat ctgggtaggc g                                  31
```

PROTEIN HAVING GLUTAMINASE ACTIVITY AND GENE ENCODING THE SAME

BACKGROUND OF THE INVENTION

1. Field of the Invention

The present invention relates to glutaminase and a glutaminase gene encoding the same, more specifically, to a protein having a glutaminase activity and excellent in salt resistance and thermostability, and a gene encoding the protein having a glutaminase activity.

2. Prior Art

Glutaminase is an enzyme which generates ammonia and L-glutamic acid which gives good taste by decomposing L-glutamine. Glutaminase has an important role in a food industry and is useful for producing, for example, soy sauce or a cooked product obtained by enzymatically decomposing protein. Glutaminase has been isolated from various kinds of biological species and its enzymological properties and the gene have been reported (e.g., Japanese Patent Publication No. 38748/1994).

In the preparation of soy sauce and the preparation of a cooked food containing a large amount of salt, glutaminase excellent in an optimum pH, salt resistance and thermostability has been desired. A group to which the present inventors have belonged has previously found a novel glutaminase which is excellent in salt resistance and thermostability, and can effectively produce a protein-hydrolyzed product (e.g., soy sauce) enriched in an amount of glutamic acid from Cryptococcus nodaensis G60 (FERM BP-6351 deposited on May 13, 1998 with the National Institute of Advanced Industrial Science and Technology, Japan) (Japanese Provisional Patent Publication No. 332553/1999 which corresponds to U.S. Pat. No. 6,063,409 herein incorporated by reference).

For further improving the property of the above enzyme by a genetic engineering means and for producing the enzyme with a large amount, it is important to obtain a gene of the enzyme.

According to the above, it is possible to improve qualities of the protein-hydrolyzed product (e.g., soy sauce) easily and provide the same with inexpensive.

SUMMARY OF THE INVENTION

An object of the present invention is to provide a protein having a glutaminase activity and excellent in salt resistance and thermostability, and a gene encoding the same.

The present inventors have earnestly investigated about the above-mentioned problems in various manners and as a result, they have succeeded in isolating a glutaminase gene derived from Cryptococcus nodaensis to accomplish the present invention.

That is, the present invention provides the following materials and process.

1. A protein shown in either of the following (a) or (b):
   (a) a protein having an amino acid sequence represented by amino acid numbers 1 to 684 shown in SEQ ID NO:2,
   (b) a protein having a glutaminase activity in which one or more amino acids is/are deleted from, substituted by, inserted to or added to the amino acid sequence of the above-mentioned (a).
2. A protein shown in either of the following (c) or (d):
   (c) a protein having an amino acid sequence represented by amino acid numbers 49 to 684 shown in SEQ ID NO:2,
   (d) a protein having a glutaminase activity in which one or more amino acids is/are deleted from, substituted by, inserted into or added to the amino acid sequence of the above-mentioned (c).
3. A gene containing DNA shown in either of the following (e) or (f):
   (e) a gene containing DNA encoding the protein according to claim 1,
   (f) a gene encoding a protein which hybridizes with the DNA of the above-mentioned (e) under a stringent condition and has a glutaminase activity.
4. A gene containing DNA shown in either of the following (g) or (h):
   (g) a gene containing DNA encoding the protein according to claim 2,
   (h) a gene encoding a protein which hybridizes with the DNA of the above-mentioned (g) under a stringent condition and has a glutaminase activity.
5. A recombinant DNA containing the gene described in the above 3 or 4.
6. A transformant or a transductant containing the recombinant DNA described in the above 5.
7. A process for producing glutaminase which comprises culturing the transformant or the transductant described in the above 6 and collecting glutaminase from a culture medium.

DESCRIPTION OF THE PREFERRED EMBODIMENTS

In the following, the present invention will be explained in detail.

1. A Protein Having a Glutaminase Activity and a Gene Encoding the Same

The protein of the present invention is a protein shown in either of the following (a) or (b).
   (a) a protein having an amino acid sequence represented by amino acid numbers 1 to 684 shown in SEQ ID NO:2,
   (b) a protein having a glutaminase activity in which one or more amino acids is/are deleted from, substituted by, inserted to or added to the amino acid sequence of the above-mentioned (a).

The protein shown in (a) can be obtained by subjecting a natural type glutaminase gene derived from a chromosomal DNA or cDNA of Cryptococcus nodaensis G60 to cloning and introducing the resulting clone into a suitable host-vector system to express the same.

Incidentally, one or plural number of the amino acids may be deleted from, substituted by, inserted into or added to the amino acid sequence of the above (a) so long as it has a glutaminase activity as shown in the above (b). In the present specification, "a plural number" generally means 2 to 300, preferably 2 to 170, more preferably 2 to 50, most preferably 2 to 10 amino acids whereas it is different depending on a position in a steric structure or a kind of the amino acid residue.

Such a mutant type glutaminase, i.e., the protein of the above (b) can be obtained by introducing variation such as substitution, deletion, insertion, addition or inversion into the base sequence of the natural type glutaminase gene to prepare a variant type glutaminase gene, and introducing the gene into a suitable host-vector system to express the same.

As a method of introducing variation into a gene, there may be mentioned, for example, a site-specific mutation introducing method, a random mutation introducing method by PCR, and a method in which a gene is selectively cleaved and then a selected nucleotide is removed or added, and the cleaved genes are linked.

The glutaminase gene of the present invention is a gene containing DNA encoding the protein of the above (a) or (b). Incidentally, the glutaminase gene of the present invention may be a gene encoding a protein having a glutaminase activity which hybridizes with the DNA encoding the protein of the above-mentioned (a) or (b) under a stringent condition. In the present specification, "a stringent condition" means, for example, a condition wherein a sodium concentration is 50 to 300 mM, preferably about 150 mM and a temperature is 42 to 68° C., preferably about 65° C.

Examples of the gene containing DNA encoding the protein of the above-mentioned (a) may include DNA containing base sequence represented by the base numbers 1 to 2052 shown in SEQ ID NO:1 in the sequence listing. This DNA is a natural type glutaminase gene.

The natural type glutaminase gene can be obtained by subjecting a natural type gene derived from a chromosomal DNA or CDNA of *Cryptococcus nodaensis* G60 to cloning. As a method of go subjecting to cloning of the gene, for example, there may be mentioned a method in which glutaminase is purified and a partial amino acid sequence is determined, then, a suitable probe DNA is synthesized and screening is carried out from the chromosomal DNA of *Cryptococcus nodaensis* by using the probe DNA. Also, there may be mentioned a method in which a suitable primer DNA is prepared based on a partial amino acid sequence, and the DNA containing a fragment of the gene is amplified by a polymerase chain reaction (hereinafter abbreviated to as "PCR method") such as the 5' RACE method and the 3' RACE method, and the resulting genes are linked to obtain DNA containing whole length gene.

In more detail, a natural type glutaminase gene can be obtained as mentioned below. First, *Cryptococcus nodaensis* is cultured, and after the resulting culture broth is lyophilized in a liquid nitrogen, it is physically ground by using a mortar, etc., to obtain fine powder state cell pieces, and chromosomal DNA is extracted from the cell pieces by the conventional manner. In the extraction operation, a commercially available DNA kit can be utilized.

Then, glutaminase is purified to determine the N-terminal amino acid sequence. Moreover, an amino acid sequence of a peptide fragment obtained by digestion using lysylendopeptidase is determined.

Glutaminase can be purified by the method as disclosed in Japanese Provisional Patent Publication No. 332553/1999. That is, *Cryptococcus nodaensis* G60 is firstly inoculated into a suitable medium to obtain a culture broth containing proliferated cells. After adding a cell wall lytic enzyme to the cells obtained by centrifugation of the culture broth, the mixture was centrifuged to obtain a supernatant. The supernatant is heated to denature impurity proteins and the resulting material is further centrifuged to remove denatured proteins.

To the above-mentioned supernatant is added acetone (−20° C.), the mixture is well stirred and after maintaining the mixture at 4° C. for 5 hours, the mixture is centrifuged to collect precipitate. The precipitate is dissolved in an acetate buffer to obtain a crude enzyme solution containing glutaminase. Moreover, a fraction having glutaminase activity is purified by using a DEAE-Sepharose column, a phenyl-Sepharose column, a hydroxyapatite column, a gel filtration column, an HPLC (high performance liquid chromatography), etc., whereby glutaminase can be purified.

Then, a primer to be used for PCR is synthesized in view of an information about a partial amino acid sequence, a codon use frequency of microorganisms belonging to Cryptococcus genus, and the like. Next, PCR is carried out by using these primers and the chromosomal DNA obtained as mentioned above as templates. Moreover, based on the base sequence of the resulting DNA, a primer is synthesized.

Next, the chromosomal DNA is treated by a restriction enzyme present at a part of a glutaminase gene region (an intron is included therein) obtained, and then, self ligation is carried out. Using the resulting material as a template, inverse PCR is carried out by using the above-mentioned primer. The base sequences of the respective DNA fragments thus obtained are ligated to obtain a glutaminase gene containing an intron which is encoded on a genome.

Next, a glutaminase gene containing no intron, i.e., cDNA encoding the glutaminase gene is obtained. First, *Cryptococcus nodaensis* G60 is cultured, and after lyophilizing the resulting cells in liquid nitrogen, the cells are ground by using a mortar, etc., to obtain fine powder state cell pieces. Then, whole RNA fractions are extracted from the cell pieces by the conventional manner. In the extraction operation, a commercially available RNA kit can be utilized.

RNA is recovered from the resulting RNA extracted solution by ethanol precipitation, and RNA having a poly-A chain may be fractionated from the recovered RNA by the conventional manner. In the fractionation operation, a commercially available Oligo dT column can be utilized.

Next, primers to be used in PCR are synthesized from an N-terminal amino acid sequence of glutaminase and an amino acid sequence of a peptide fragment obtained by digestion using lysylendopeptidase. By using this primer DNA and the RNA obtained as mentioned above, DNA's containing fragments of the gene are amplified by a suitable RT-PCR reaction such as the 5' RACE method and the 3' RACE method, and ligated these to obtain DNA containing whole gene. In the partial cDNA synthesis operation by the 5' RACE method and the 3' RACE method, a commercially available kit can be utilized.

DNA is amplified by using the above-mentioned cDNA as a template and subjecting to PCR using synthetic primers complementary to the 5'-terminus sequence and the 3'-terminus sequence. The amplified DNA can be subjected to cloning according to the conventional manner.

A recombinant DNA can be obtained by inserting the amplified DNA into a suitable vector. In the cloning, a commercially available kit such as TA Cloning Kit (trade name, available from Invitrogen Co.), a commercially available plasmid vector DNA such as pUC119 (trade name, available from Takara Shuzo Co.), pBR322 (trade name, available from Takara Shuzo Co.), pBluescript SK$^+$ (trade name, available from Stratagene Co.), a pCR2.1-TOPO vector using TOPO TA Cloning Kit (trade name, manufactured by Invitrogen Co.), etc., and a commercially available bacteriophage vector DNA such as λEMBL3 (trade name, available from Stratagene Co.), etc. can be used.

By using the resulting recombinant DNA, a transformant or a transductant can be obtained by transforming or transducing a host cell therein, respectively. Transformation can be carried out, for example, by the method of D. M. Morrison (Method in Enzymology, 68, 326–331, 1979). Also, transduction can be carried out, for example, by the method of B. Hohn (Method in Enzymology, 68, 299–309, 1979).

As a host cell, microorganisms such as *Escherichia coli* (K-12, *Escherichia coli* JM109 (trade name, available from Takara Shuzo Co.), XL-Blue (trade name, available from Funakoshi Co.)), yeast (INVSc1 (trade name, available from Invitrogen Co.), filamentous fungi, actinomycetes, etc., and animal cells can be used.

The whole or total base sequence (see SEQ ID NO:1) of the DNA amplified as mentioned above can be analyzed by using, for example, LI-COR MODEL 4200L sequencer (trade name, manufactured by LI-COR, Inc.), 370 DNA sequence system (trade name, manufactured by Perkin-Elmer Co.), and the like. By comparing the base sequence with an information of a partial amino acid sequence, it can be confirmed whether a natural type glutaminase gene can be obtained or not.

According to the analyses of the natural type glutaminase gene, translated polypeptide, i.e., an amino acid sequence of the protein as mentioned (a) can be fixed.

In another embodiment, the glutaminase of the present invention is a protein shown in either of the following (c) or (d).
   (c) a protein having an amino acid sequence represented by amino acid numbers 49 to 684 shown in SEQ ID NO:2,
   (d) a protein having a glutaminase activity in which one or more amino acids is/are deleted from, substituted by, inserted into or added to the amino acid sequence of the above-mentioned (c).

The protein shown in (c) is a protein found by the present inventors to present in a glutaminase purified standard product of *Cryptococcus nodaensis*. This protein can be obtained by introducing variation of deletion into the base sequence of the natural type glutaminase gene to prepare a variant type glutaminase gene which encodes an amino acid sequence shown by the amino acid numbers 49 to 684 of SEQ ID NO:2, and introducing the same into a suitable host-vector system to express the same.

The variant type glutaminase gene encoding the protein shown in (c) can be specifically prepared by the method as mentioned below.

A sense primer is synthesized in a form of linking abase sequence encoding a protein with amino acid numbers 49 to 684 of SEQ ID NO:2 to the downstream of the known signal sequence. Then, an antisense primer which complements to the base encoding the C-terminal amino acid sequence is synthesized. To the 5'-terminuses of the respective primers, suitable restriction enzyme recognition sites are added in a form that their frames are adapted thereto. The amplified fragments are incorporated into the cloning vector as described above. According to the above procedure, a variant type glutaminase gene encoding the protein shown in (c).

Incidentally, in the protein, as shown in (d), one or a plural number of amino acids may be deleted, substituted, inserted or added in the amino acid sequence of (c) so long as it has a glutaminase activity. The protein shown in (d) can be obtained by introducing variation of deletion into the base sequence of DNA encoding the natural type glutaminase gene or the protein shown in (c) to prepare a variant type glutaminase gene, and introducing the gene into a suitable host-vector system to express the same.

As an example of the gene containing DNA encoding the protein shown in the above (c), there may be mentioned DNA containing a base sequence shown by the base numbers 145 to 2052 of SEQ ID NO:1 in the Sequence Listing. Incidentally, the glutaminase gene of the present invention may be a gene which hybridizes with the DNA encoding the protein having a glutaminase activity of the above-mentioned (c) or (d) under a stringent condition.

2. Preparation Method of Glutaminase

When the glutaminase of the present invention is to be prepared, a recombinant DNA containing the glutaminase gene is firstly prepared. Then, a transformant or a transductant containing the recombinant DNA is prepared and cultured, and glutaminase is collected from a culture medium.

To produce the protein having a glutaminase activity by using the glutaminase gene of the present invention, it is necessary to select a suitable host-vector system. Such a system may include a system of yeast expression vector pYES2 (trade name, available from Invitrogen Co.) and yeast (*Saccharomyces cerevisiae*), a system of *Escherichia coli* expression vector pTE (trade name, available from Stratagene Co.) and *Escherichia coil* (*E. coli*) and the like. The system of yeast is preferably used in the point that saccharide chain addition to the protein occurs.

The recombinant DNA can be obtained by inserting the glutaminase gene into a suitable vector. As the vector, there may be used, for example, yeast expression vector pYES2, pYD1 (both trade names, available from Invitrogen Co.), pAUR123 (trade name, available from Takara Shuzo, Co.), pYEX-BX, pYEX-S1, PYEX-4T (all trade names, available from CLONETECH Co.), YEpFLAG-1 (trade name, available from SIGMA Co.), *Escherichia coli* expression vector pSET (trade name, available from Invitrogen Co.), pTE (trade name, available from Stratagene Co.), and the like.

Then, the recombinant DNA is transformed or transduced in a host cell. Transformation into yeast can be carried out, for example, by the method of D. M. Becker et al. (Method in Enzymology, 194, 182–187, 1991). Transformation into *Escherichia coli* can be carried out, for example, by the method of B. Hohn (Method in Enzymology, 68, 299–309, 1979). As a host cell, microorganisms such as *Escherichia coli*, yeast, filamentous fungi, actinomycetes, etc., and animal cells can be used.

According to the above procedure, a transformant or a transductant having an ability of producing glutaminase can be obtained. To culture the transformant or the tranductant, they may be cultured by the usual solid culture method, and a liquid culture method is preferably used if the situation allows.

When yeast is used as a host cell, as a medium, a generally employed nutrient-rich medium such as YPD medium and YM medium can be used. Also, when a selective medium is used depending on the genetic properties of the host cell, a SD medium which is the minimum medium can be used. When the selective medium is used, a selective pressure varies depending on the selected vector-host system to be used so that an amino acid(s), a nucleic acid(s) and the like other than the selective pressure is/are added to the minimum medium depending on the genetic requirements of the host cell.

In addition, an inorganic salt(s), a starting material of saccharide(s), vitamin(s) and the like may be optionally added to the medium, depending on necessity. Incidentally, an initial pH of the medium is preferably adjusted to pH 6 to 9. Moreover, some of the vectors can control expression of a protein. When these vectors are used, an inducer corresponding to the vector, such as galactose, a copper ion, etc., is added to the medium whereby glutaminase can be induced.

When yeast is cultured, culture is carried out at 25 to 35° C., preferably about 30° C. for 24 to 48 hours by an aeration stirring deep culture, shaking culture, standing culture, and the like.

Incidentally, the genetic engineering method in the present invention can be carried out, for example, according to the descriptions such as "Molecular Cloning: A Laboratory Manual 2nd Edition" (1989), Cold Spring Harbor Laboratory Press, ISBN 0-87969-309-6, "Current Protocols in Molecular Biology" (1989), John Wiley & Sons, Inc. ISBN 0-471-50338-X, etc.

EXAMPLES

In the following, Examples of the present invention will be explained more specifically, but the present invention is not limited by these.

Example 1

Cloning of Glutaminase Gene (1) Extraction of Chromosomal DNA from *Cryptococcus nodaensis*

*Cryptococcus nodaensis* G60 (FERM BP-6351) was cultured and after 1 g of the obtained microorganisms were frozen in liquid nitrogen, it was physically ground in a mortar to obtain cell particles in a fine powdery form. From this cell particles, genomic DNA was extracted by using a nucleic acid extracting reagent SepaGene (trade name, manufactured by Sanko Junyaku Co., Japan). The whole operation was carried out according to the protocol attached to the reagent.

(2) Determination of Amino Acid Sequences of an N Terminus and Inner Part of Glutaminase Glutaminase produced by *Cryptococcus nodaensis* G60 was purified according to a method described in Japanese Provisional Patent Publication No.332553/1999. That is, *Cryptococcus nodaensis* G60 was inoculated into a culture medium comprising 3.0% of glucose, 0.5% of yeast extract, 0.1% of $KH_2PO_4$ and 0.1% of $MgSO_4$ with a pH of 5.5, and cultured under shaking for 4 days at 25° C. to obtain a seed culture. This seed culture was inoculated into 15 liters of the culture medium having the same composition as the above, and it was cultured for 30 hours at 25° C. in a 30 liter-volume of a jar fermenter at an aeration rate of 20 liter/min and at a stirring rate of 300 rpm, to obtain a culture broth containing the grown cells.

The culture broth containing the grown cells was subjected to centrifugal separation, and 200 g of the thus obtained microbial paste was collected, added thereto 2.0 litters of 2.0M of acetate buffer (pH 5.0) and suspended well therein. Subsequently, as cell wall lytic enzyme, 16 g of Cellurase Onozuka R-10 (manufactured by Yakult Honsha Co., Ltd.) was added thereto, and the resultant mixture was stirred for 12 hours at 42° C., followed by a centrifugal separation (8,000 rpm, 20 minutes) to give a supernatant. The supernatant was heated for one hour at 60° C., and after adjusting the pH to 7.0 by 0.2M $K_2HPO_4$, it was further heated for one hour at 60° C. to denature impure proteins and the thus denatured proteins were removed by centrifugation (8,000 rpm, 20 minutes).

To the above-mentioned supernatant, 2-fold volumes of acetone (−20° C.) were added and the mixture was well stirred, and then, after kept at 4° C. for 5 hours, it was subjected to centrifugation (8,000 rpm, 20 minutes) to collect precipitates. This precipitates were dissolved in 0.02 M acetate buffer (pH 6.0), and it was dialyzed against 0.02 M acetate buffer (pH 6.0). The crude enzyme solution mentioned above was applied to a DEAE-Sepharose CL-6B column (trade name, manufactured by Pharmacia Co.) previously equilibrated by 0.02 M acetate buffer (pH 6.0), to let the enzyme adsorbed. The enzyme was washed sufficiently with 0.02M acetate buffer (pH 6.0), and eluted with gradient of 0 to 0.5M NaCl, to collect an active fraction(s).

Subsequently, after this enzyme solution was dialyzed against 0.1M acetate buffer containing each of 0.5M ammonium sulfate and 20% (w/v) ethylene glycol, it was adsorbed to a Phenyl-Sepharose column (trade name, manufactured by Pharmacia Co.) previously equilibrated with the same buffer solution as above, washed with the same buffer solution, and then, the enzyme was eluted with a gradient of both 0.5–0M ammonium sulfate and 20–60% ethylene glycol, to collect an active fraction(s). The obtained enzyme solution was concentrated with an ultra-filtration unit (fractional molecular weight of 10,000, manufactured by Amicon Co.), and then, it was dialyzed against 0.02M phosphate buffer (pH 6.0). This enzyme solution was adsorbed onto a hydroxyapatite column (manufactured by Nakarai Tesque, Inc.) previously equilibrated with 0.02M phosphate buffer (pH 6.0) and washed with the same phosphate buffer. Then, the enzyme was eluted with a gradient of 0.02–0.3M phosphate to collect an active fraction(s). Repeatedly, the enzyme solution was concentrated using the same ultrafiltration unit as above.

The concentrated enzyme solution was applied to a column (1.2×100 cm) filled with Sephacryl S-300 (trade name, manufactured by Pharmacia Co.) that had been equilibrated with 0.1M phosphate buffer (pH6.0) containing 0.2M of NaCl for gel filtration. The obtained active fractions were concentrated with Centricon (trade name, manufactured by Pharmacia Co., fractional molecular weight of 30,000) and the enzyme solution was separated by HPLC using TSK gel G3000SW (trade name, manufactured by Tosoh Co.) to give a homogeneous enzyme preparation.

Analysis on an N-terminus amino acid sequence of glutaminase was conducted by Toray Research Center using 500 μg of the purified glutaminase sample. As a result of N-terminus analysis, it was found that there were existed tree kinds of proteins in the sample. Further, it was found that purification was not satisfactory carried out by the above method to strictly perform an analysis on the N-terminus amino acid sequence.

From the information of the above-obtained analysis on the N-terminus amino acid sequence and information of the later-described DNA sequence of chromosomal DNA, it was assumed that N-terminus amino acid sequences of the 3 kinds of proteins were as shown in SEQ ID NO:3, 4 and 5.

Initially, from this result and the molecular weight of the enzyme obtained from gel filtration, it was assumed that glutaminase was a hetero trimer comprising three different subunits. Therefore, it was concerned that three kinds of proteins had to be separately cloned and since the total size of the gene is large, cloning of the gene is extremely difficult due to an instability of the gene itself even though the cloning is completed.

However, as described later, those fragments were derived from the same protein. It was concluded that these were the result of a partial digestion by a protease contained in the used cellulase, the result of a partial digestion by a protease existing in a purification process, or the result of difference in localization in vivo.

Analysis on a partial amino acid sequence of the inner part of glutaminase was carried out as mentioned below. 400 μg of the purified glutaminase sample was digested in 500 μl of 50 mM tris-HCl buffer solution (pH 9.0) containing 1 μg of lysyl-endopeptidase (available from Wako Junyaku Kogyo Co.) and 0.3% SDS at 37° C. for 16 hours. This enzymatically digested solution was applied to Shimadzu HPLC system (manufactured by Shimadzu Seisakusho Co., column: Asahipak ODP-5E) and the resulting peptide fragments were purified. Amino acid sequences of the above peptide fragments were analyzed by Edman method using Protein Sequencer (Type 492, trade name, manufactured by Applied Biosystem Co.). Amino acid sequences of the four kinds of peptide fragments were shown in SEQ ID NO: 6, 7, 8 and 9.

(3) Amplification of Partial Fragment of Glutaminase Gene by PCR Method

From the partial amino acid sequences of glutaminase determined in (2), primers represented by SEQ ID NO: 10 to 13 were designed and subjected to DNA syntheses.

That is, a sense mix primer represented by SEQ ID NO:10 corresponding to a peptide sequence represented by SEQ ID NO:6, a sense mix primer represented by SEQ ID NO:11 and an antisense mix primer represented by SEQ ID NO:12 corresponding to a peptide sequence represented by SEQ ID NO:7, and an antisense mix primer represented by SEQ ID NO:13 corresponding to a peptide sequence represented by SEQ ID NO:8 were synthesized, respectively. Using those primers, PCR reaction was carried out. For the reaction, Ex taq polymerase (trade name, manufactured by Takara Shuzo Co.) was used and conditions for the reaction mixture was set according to the protocol attached to the polymerase.

PCR reaction was carried out by Robocycler GRADIENT 96 (trade name, manufactured by Stratagene Co.). The basic reaction conditions were, for denature, 94° C. for 0.5 minute, for annealing, 42 to 58° C. for 0.5 minute and for elongation reaction, 72° C. for 3 minutes, those steps making one cycle, which was repeated for 45 cycles. The annealing temperature was gradually elevated from 42 to 58° C.

Using the chromosomal DNA obtained in (1) as a template, there were detected amplifications of specific DNA fragments corresponding to about 1.6 kbp in the PCR reaction combining the primer of SEQ ID NO:10 and the primer of SEQ ID NO:12, about 1.8 kbp in the PCR reaction combining the primer of SEQ ID NO:10 and the primer of SEQ ID NO:13, and about 0.2 kbp in the PCR reaction combining the primer of SEQ ID NO:11 and the primer of SEQ ID NO:13, respectively. From these facts, it was expected that peptides were aligned in order of SEQ ID NO:6-SEQ ID NO:7-SEQ ID NO:8 inside glutaminase.

However, amplification efficiency of the specific DNA fragment was shown best for one of 1.6 kbp, and in others, there were identified a slight degree of amplifications of non-specific DNA fragments other than the specific DNA fragments. Therefore, hereinafter, the DNA fragment of 1.6 kbp was chosen for DNA sequence analysis.

(4) Determination of DNA Sequence of the Amplified DNA Fragment

The above-mentioned amplified DNA fragment of 1.6 kbp was collected from a gel after 0.7% agarose gel electrophoresis, and this was inserted in a pCR2.1-TOPO vector using TOPO TA Cloning Kit (trade name, manufactured by Invitrogen Co.). The obtained recombinant plasmid (hereinafter referred to as pTKgln1.6) was subjected to a sequence reaction using Thermo Sequenase Cycle Sequencing Kit (trade name, manufactured by Amersham Pharmacia Biotech Co.) and analyzed for its base sequence using LI-COR MODEL 4200L Sequencer (trade name, manufactured by Aroca Co.). The sequence reaction was carried out according to the protocols attached to the materials.

As a result, base sequence encoding amino acid residues not corresponding to the primer synthesis in the peptide sequence of SEQ ID NO:6 was identified and there were found the base sequences encoding each of SEQ ID NO:6, 7 and 9 in the obtained base sequence. It was concluded from these facts that the amplified DNA fragment was a part of the gene encoding a target glutaminase. However, the peptide of SEQ ID NO:8 was not identified.

(5) Southern Blotting Analysis of Chromosomal DNA of *Cryptococcus nodaensis*

Next, 3 μg of the chromosomal DNA prepared in Example 1-(1) was digested for 16 hours at 37° C. using each 100 units of restriction enzymes BamHI, EcoRV, HindIII, NruI, NotI, SacI, SalI, StuI and XhoI. Those restriction enzymes make one or two cleavages in the amplified DNA fragment. The resultant DNAs digested by the restriction enzymes were subjected to 0.7% agarose gel electrophoresis. After the electrophoresis, using Southern blot technique, DNA was transcribed to a nylon membrane (Hybond-N+, trade name, manufactured by Amersham Pharmacia a Biotech Co.). As a probe for hybridization, the one amplified by PCR using pTKgln1.6 as a template and SEQ ID NO: 14 and 15 as primers, in the presence of PCR DIG labeling mix (trade name, manufactured by Roche Diagnostics Co.) was used. Reaction conditions for PCR were set similarly to those in the above described (3), except for carrying out elongation reaction at 72° C. for 2 minutes and repeating the reaction cycle for 30 cycles.

After washing the above mentioned nylon membrane with 2×SSC (0.3M NaCl, 0.03M sodium citrate, pH 7.0), analysis was carried out using DIG system according to a user's manual (manufactured by Roche Diagnostics Co.).

As a result, signals from the hybridized probes were detected at locations corresponding to the DNA length of about 3.0 kbp and about 2.5 kbp for BamHI digestion, about 4.5 kbp and about 2.5 kbp for EcoRV digestion, about 6.0 kbp and about 1.0 kbp for HindIII digestion, about 2.5 kbp and about 1.8 kbp for NruI digestion, about 5.0 kbp and about 3.0 kbp for NotI digestion, about 1.8 kbp and about 0.8 kbp for SacI digestion, about 2.0 kbp and about 0.8 kbp for SalI digestion, about 6.0 kbp and about 1.3 kbp for StuI digestion and about 2.0 kbp and about 0.5 kbp for XhoI digestion, respectively.

(6) Recovery of Partial Fragment of Glutaminase Gene by Inverse PCR

Based on the above results, inverse PCR was carried out using EcoRV fragment of about 2.5 kbp and SalI fragment of about 2 kbp. 3 μg of chromosomal DNA digested by EcoRV and SalI was isolated by 0.7% agarose gel electrophoresis, and then, gels were cut out at the site corresponding to each of the sizes (about 2.5 kbp for EcoRV and about 2.0 kbp for SalI). From the gel, DNA fragments was extracted and purified using QIA quick Gel Extraction Kit (trade name, manufactured by QIAGEN Co.), and the DNA fragments were subjected to self-ligation using DNA Ligation Kit Ver.2 (trade name, manufactured by Takara Shuzo Co.). Using the above ligation products as templates, inverse PCR was carried out according to the conventional method.

As primers for PCR, combination of SEQ ID NO:16 and SEQ ID NO:17 were used in case of using EcoRV fragment as a template, and combination of SEQ ID NO:18 and SEQ ID NO:19 were used in case of using SalI fragment as a template. For PCR reaction, Ex taq polymerase (trade name, manufactured by Takara shuzo Co.) was used, and reaction conditions were set according to the protocol attached to the polymerase. PCR was carried out by Robocycler GRADIENT96 (trade name, manufactured by Stratagene Co.).

The basic reaction conditions for PCR were, for denature, 94° C. for 0.5 minute, for annealing, 48 to 59° C. for 0.5 minute, and for elongation reaction, 72° C. for 3 minutes (when using EcoRV fragment as a template) and 2 minutes (when using SalI fragment as a template), those steps making one cycle, which was repeated for 30 cycles. The annealing temperature was gradually elevated from 48 to 59° C. Each of the amplified DNA fragments was collected from a gel after completion of agarose gel electrophoresis, and this was inserted in a pCR2.1-TOPO vector using TOPO TA Cloning Kit (both trade names, manufactured by Invitrogen Co.). The obtained recombinant plasmid was subjected to a sequence reaction using Thermo Sequenase Cycle Sequencing Kit (manufactured by Amersham Pharmacia Biotech Co.) and analysis of its base sequence was carried out by using LI-COR MODEL 4200L Sequencer (trade name, manufactured by Aroca Co.). As a result, from EcoRV fragment, further 3' downstream region of the 1.6 kbp DNA fragment obtained in (3) and from SalI fragment, further 5' upstream region thereof were identified. In addition, from 3' downstream region, base sequence encoding a peptide fragment of SEQ ID NO:8 was found which had not been formerly found. Therefore, it was confirmed that in this about 6.0 kbp DNA fragment in which the 1.6 kbp DNA fragment obtained in (3) and the 2.5 kbp and 2.0 kbp DNA fragments obtained in (6) had been all linked, the gene encoding glutaminase was contained.

Example 2

Preparation of Glutaminase cDNA (1) Extraction of Whole RNA from *Cryptococcus nodaensis*

*Cryptococcus nodaensis* was inoculated into 100 ml of raw soy sauce medium (6% of millet jelly, 16% of raw soy sauce, 0.1% of $MgSO_4$ and 0.1% of $KH_2PO_4$, pH 6.0), and cultured for 30 hours at 25° C. After completion of culture, the resultant culture broth was centrifuged to collect the cell bodies. About 500 mg of the cells among the resultant culture broth were frozen in liquid nitrogen and physically ground in a mortar to obtain cell particles in a powdery form. From this cell particles, total RNA was extracted using RNeasy Plant mini Kit (trade name, manufactured by QIAGEN Co.). The whole operation was carried out according to the protocol attached to the Kit.

(2) Preparation of Glutaminase cDNA Using RACE Method

The above obtained total RNA was used to confirm amplification of about 1 kbp DNA fragment corresponding to 5'-site region of glutaminase cDNA and about 2 kbp DNA fragment corresponding to 3'-site region of glutaminase cDNA using First Choice RLM-RACE Kit (trade name, manufactured by Ambion Co.) and 3'-Full RACE Core Set (trade name, manufactured by Takara Shuzo Co.), respectively. The whole operation was carried out according to the protocols attached to the materials. Primers used for First Choice RLM-RACE Kit and for 3'-Full RACE Core Set were shown in SEQ ID NO:20 and 21, respectively. The thus amplified DNA fragments were cloned to confirm their DNA sequences in the same manner as in Example 1-(4).

Then, using the data of First Choice RLM-RACE Kit (trade name, Ambion Co.) on an information of the base sequence at 5'terminus, a sense primer complementary to 5' terminus base sequence of glutaminase cDNA was synthesized as shown in SEQ ID NO:22. Using the above 3'-Full RACE Core Set (trade name, manufactured by Takara Shuzo Co.), whole glutaminase cDNA was amplified (about 2 kbp) using SEQ ID NO:22 primer in place of SEQ ID NO:21 primer, and SEQ ID NO:23 primer in place of an adapter primer attached to the kit.

The thus amplified DNA fragment was inserted into a pCR2.1-TOPO vector using TOPO TA Cloning Kit (trade name, manufactured by Invitrogen Co.) to obtain a recombinant DNA (plasmid pTKgln).

From analysis on base sequences of the DNA fragment inserted into plasmid pTKgln, it was found that the DNA fragment contained glutaminase gene represented by base numbers 1 to 2052 shown in SEQ ID NO:1. Base numbers 1 to 2052 of SEQ ID NO:1 represent a coding region and base numbers 2053 to 2055 are a stop codon. An amino acid sequence of a polypeptide translated from the glutaminase gene is shown in SEQ ID NO:2. In comparison under consideration of introns, it was confirmed that the DNA sequence of SEQ ID NO:1 well coincides with the base sequence of the previously shown chromosomal glutaminase gene. In the amino acid sequence of the polypeptide translated from the DNA sequence of SEQ ID NO:1, all of the N-terminus polypeptides represented by SEQ ID NO:3 to 5, and the partial amino acid sequences of inner part represented by SEQ ID NO:6 to 9 were identified.

From these results, it was elucidated that three peptide fragments obtained by N-terminus analysis were, as stated above, those derived from the same protein that was partially digested, and that glutaminase is not a trimer of different kinds of proteins as initially expected, but a trimer comprising proteins encoded in the same gene. In addition, it was assumed that an amino acid sequence comprising amino acid numbers 49 to 684 of SEQ ID NO:2 was glutaminase in which signal sequence was deleted.

From the DNA—DNA homology search, the glutaminase of the present invention showed low homology to the known glutaminase, therefore, it was assumed that it is a novel glutaminase gene.

The plasmid pTKgln containing the whole glutaminase cDNA, that is, the base sequence represented by the base numbers 1 to 2052 of SEQ ID NO:1 is deposited as FERM BP-7292 with the National Institute of Advanced Industrial Science and Technology, Japan.

Example 3

Expression of Glutaminase cDNA (1) Expression of the Whole Glutaminase cDNA

The whole glutaminase cDNA (the DNA sequence represented by the base numbers 1 to 2052 of SEQ ID NO:1) was expressed according to the method mentioned below. This cDNA encodes an amino acid sequence represented by the amino acid numbers 1 to 684 of SEQ ID NO:2.

The whole glutaminase cDNA was amplified using the above-mentioned plasmid pTKgln as a template, and using primers of SEQ ID NO:24 and 25, respectively, obtained by inserting Kpn I site immediately before the start Met codon and obtained by inserting EcoR I site immediately after the stop codon. The amplified DNA was digested enzymatically by the restriction enzyme EcoR I and Kpn I (both available from Takara shuzo Co.), and then, it was applied to 0.7% agarose gel electrophoresis. DNA fragments contained in the gel corresponding to the target size (about 2 kbp) was cut out and purified.

Subsequently, the above-obtained DNA fragment was inserted into a yeast expression vector pYES2 (trade name, manufactured by Invitrogen Co.) treated enzymatically with the same restriction enzymes, to prepare a plasmid pYES-TKgln. By using the above plasmid, expression of the target protein (glutaminase) can be induced and expressed by galactose. As a host yeast (*Saccharomyces cerevisiae*), INVSc1 available from Invitrogen Co. (genotype: MATa, his3Δ1, leu2, trp1-289, ura3-52/MATα, his3Δ1, leu2, trp1-289, ura3-52) was used. By the lithium acetate method, the host yeast was transformed by the above plasmid pYES-TKgln. As a selection medium, 0.67% Yeast Nitrogen base without amino acids (available from Difco Co.), 2% raffinose (available from Wako Junyaku Kogyo Co.), 0.01% adenine, arginine, cysteine, leucine, lysine, threonine, tryptophan, 0.005% aspartic acid, histidine, isoleucine, methionine, phenylalanine, proline, serine, tyrosine and valine (all available from Kanto Kagaku Co.) were used. The lithium acetate method was carried out according to the description in "Kaiser C. Michael is S, Mitchell A: Lithium acetate yeast transformation, Methods in Yeast Genetics, A cold Spring harbor Laboratory Course Manual 1994 edition (Cold Spring Harbor Laboratory press, pp. 133–134, 1994)".

Then, using the obtained transformant, protein was expressed according to the protocol attached to the pYES2 vector. The transformant was inoculated in 20 ml of selection medium in a 200 ml baffled Erlenmeyer flask, and cultured under shaking at 30° C. at 140 rpm for about 14 hours to give seed culture. Turbidity ($OD_{600}$) of the seed culture was measured and the seed culture was inoculated into a protein expression inducing medium so that the initial turbidity was $OD_{600}$=0.4. A 500 ml Sakaguchi flask was used for a culture by protein expression inducing medium, and the seed culture was cultured under shaking in 50 ml of medium at 30° C. at 140 rpm. For the protein expression inducing medium, 1% raffinose and 2% galactose (available from Wako Junyaku Kogyo Co.) were used as carbon sources in a selection medium.

Glutaminase activity was measured by partly modifying the method described in Japanese Provisional Patent Publication No. 332553/1999. That is, to 250 µl of 2% (w/v) L-glutamine solution were added 500 µl of 0.2M phosphate buffer (pH 6.5) and 250 µl of an enzyme solution, and the mixture was reacted at 37° C. for 30 minutes, and then the reaction was terminated by adding 250 µl of 0.75N perchloric acid solution, and 125 µl of 1.5N sodium hydroxide solution was added thereto to neutralize the reaction mixture. The above reaction mixture was then centrifuged (10,000 rpm, 10 minutes). To 100 µl of the resultant supernatant were added 1.0 ml of 0.1M hydrochloric acid-hydroxylamine buffer (pH 8.0), 1.0 ml of 20 mMNAD$^+$ solution (manufactured by Oriental Yeast Co.), and 50 µl of 500 U/ml L-glutamate dehydrogenase solution, and the mixture was reacted at 37° C., for 30 minutes and the absorbance at 340 nm was measured with a spectrophotometer. An amount of the enzyme forming 1 µmol of glutamic acid per one minute under the above conditions is determined as 1 unit (U).

The results from the measurements of enzyme activity of the above transformed yeast are shown in Table 1. The values in the table represent an glutaminase activity (mU/ml) per 1 ml of the culture broth after 32 hours of protein expression and induction. The term "vector" means a transformant by plasmid pYES2, "TK-GLN" means a transformant by plasmid pYES-TKgln. Additionally, (−) means the cells were cultured in a medium not containing galactose without inducing protein expression, and (+) means they were cultured in a protein expression inducing medium containing galactose.

It was shown that the transformant by the plasmid pYES-TKgln cultured in a protein expression inducing medium containing galactose had an increased glutaminase activity as compared to the transformant by the plasmid pYES2. It also exhibited an increased glutaminase activity when compared to the case where the transformant by plasmid pYES-TKgln was cultured in a medium not containing galactose without inducing protein expression. Glutaminase activity of the transformant by plasmid pYES-TKgln was observed on the cell surface as in the case of *Cryptococcus nodaensis* G62 strain.

TABLE 1

| Vector (−) | Vector (+) | TK-GLN (−) | TK-GLN (+) |
| --- | --- | --- | --- |
| 3.03 | 4.14 | 3.37 | 20.4 |

From the above, It was shown that an amino acid sequence (represented by amino acid numbers 1 to 684 of SEQ ID NO:2) encoded by base numbers 1 to 2052 of SEQ ID NO:1 has a glutaminase activity.

(2) Expression of a Gene Encoding a Glutaminase with Deletion of Amino Acid Numbers 1–48 at N-terminus A glutaminase gene encoding a glutaminase in which amino acid numbers 1 to 48 of N-terminus were deleted (DNA sequence represented by base numbers 145 to 2052 of SEQ ID NO:1) was expressed by a method described below. This cDNA encodes an amino acid sequence represented by amino acid numbers 49 to 684 of SEQ ID NO:2. This amino acid sequence was named to as "TKGLN-M".

FLAG expression vector YEpFLAG-1 (available from SIGMA CO.) was used as an expression vector, and the above-mentioned INVSc was used as a host. Initially, using the above plasmid pTKgln as a template, cDNA was amplified by using primers of SEQ ID NO: 26 and 27, respectively, obtained by inserting EcoR I site immediately upstream of the 49$^{th}$ glycine residue and by inserting Sac II site immediately after the stop codon, in accordance with a frame of the signal sequence derived from the expression vector.

For PCR reaction, Tbr EXT Polymerase (available from Finzyme Co.) was used and the reaction conditions were set according to the protocol attached to the polymerase. The PCR products were treated with restriction enzymes such as EcoR I (available from Takara Shuzo Co.) and Sac II (available from NEB Co.) and inserted into YEpFLAG-1 that had been treated in the same manner, to prepare a plasmid pFLAGTKgln-M. The thus obtained pFLAGTKgln-M was introduced into a host yeast INVSc by the lithium acetate method. As a selection medium, 0.67% Yeast Nitrogen base without amino acids, 2% glucose, YEAST SYNTHETIC DROPOUT MEDIUM SUPPLEMENT without tryptophan (available from SIGMA Co.) were used. For a medium inducing protein expression, YPHSM medium comprising 1% glucose, 3% glycerol (available from Wako Junyaku Kogyo Co.), 1% Yeast Extract (available from Difco Co.), 8% Peptone and 20 mM $CaCl_2$.

Then, using the obtained transformant, protein was expressed according to the protocol attached to the YEpFLAG-1 vector. The transformant was inoculated in 20 ml of selection medium in a 200 ml baffled Erlenmeyer flask, and cultured under shaking at 30° C. and 140 rpm for about 30 hours to give seed culture. 2.5 ml each of the seed culture was inoculated in 50 ml of a protein expression inducing medium in a 500 ml Sakaguchi flask, and cultured under shaking at 30° C. and 140 rpm for about 72 hours. Glutaminase activity was measured according to the above method.

For positive control, a protein "TKGLN-F" in which the amino acid sequence represented by amino acid numbers 2 to 684 of SEQ ID NO:2 had been linked to downstream of the signal sequence derived from an expression vector was prepared according to the same method. A plasmid obtained by incorporating cDNA which encodes the protein "TKGLN-F" into YEpFLAG-1 was named to as a plasmid pFLAGTKgln-F.

The results from measurement of enzyme activity of the above-obtained transformant are shown in Table 2. The values in the table represent glutaminase activity (mU/ml) per 1 ml of the culture broth after 72 hours of protein expression induction. The term "vector" means a transformant by plasmid YEpFLAG-1, "TKGLN-M" means a transformant by plasmid pFLAGTKgln-M, and the term "TKGLN-F" means a transformant by plasmid pFLAGTKgln-F.

It was shown that the transformed cell by the plasmid pFLAGTKgln-M had an increased glutaminase activity as compared to the transformant by the plasmid YEpFLAG-1 when they were cultured in protein expression inducing media containing galactose. In comparison with a transformant by plasmid pFLAGTKgln-F to which a gene encoding a protein comprising amino acid numbers 2 to 684 of SEQ ID NO:2 was inserted into the downstream of the signal sequence derived from YEpFLAG-1 as a positive control, the transformant by the plasmid pFLAGTKgln-M showed a higher glutaminase activity In an amino acid sequence of amino acid numbers 2 to 684 of SEQ ID NO:2, there exists a signal sequence of glutaminase itself. On the other hand, a protein derived from the plasmid pFLAGTKgln-F was supposed to have two signal sequences, one of which is derived from the expression vector and the other derived from itself. Therefore, it was expected that processing was not carried out properly, and protein expression or structure stability was negatively influenced, thereby leading to a lowered glutaminase activity derived from plasmid pFLAGTKgln-F.

Glutaminase activity was observed on the cell surface as in the case of the above pYES2 vector.

TABLE 2

| Vector | TKGLN-M | TKGLN-F |
|--------|---------|---------|
| 4.97   | 78.6    | 26.2    |

From the above, it was shown that an amino acid sequence (represented by the amino acid numbers 49 to 684 of SEQ ID NO:2) encoded by the base numbers 145 to 2052 of SEQ ID NO:1 has a glutaminase activity.

When a protein is synthesized by using a host-vector system, it is effective to utilize a signal peptide derived from a host cell. In case of mass expression of the glutaminase gene of the present invention using a host organism other than microorganisms belonging to Cryptococcus genus, it was shown that expression efficiency is increased by linking a gene encoding a glutaminase with a deletion of 48 amino acid residues at N-terminus to the downstream of a signal peptide derived from the host cell.

In addition, not only in the case of using Cryptococcus genus as a host but also in the case of using yeast, the glutaminase expression from the gene was localized on the surface of the cell bodies. These characteristics were due to the amino acid sequence of the protein translated from the gene of the present invention. In a mass production of the glutaminase of the present invention, it is very advantageous that the protein can be easily concentrated by collecting the cells.

According to the present invention, there were provided glutaminase and a glutaminase gene encoding the same. In addition, there were provided a recombinant DNA containing the glutaminase gene, and a transformed or transduced cell containing the recombinant DNA. Further, by the present invention, there was provided a method for producing glutaminase comprising culturing the above transformed or transduced cell and collecting glutaminase from the culture product.

The glutaminase of the present invention has a significant effect on improving product quality in production of flavoring foods containing a large amount of soy sauce and salt. In addition, use of the glutaminase gene of the present invention enables a further modification of the function of the enzyme by means of recombinant DNA technology and constructing a method for mass production of this enzyme. It is concluded that the present invention is extremely useful in industry.

What is claimed is:

1. An isolated nucleic acid comprising a nucleotide sequence selected from the group consisting of:
   (a) a nucleotide sequence encoding an amino acid sequence comprising amino acids 1 to 634 of SEQ ID NO:2, and
   (b) a nucleotide sequence, the complement thereof which binds to said nucleotide sequence (a) under stringent hybridization conditions of a sodium concentration of 50–300 mM and a temperature of 42–68° C., wherein said nucleic acid encodes a protein having glutaminase activity.

2. An isolated nucleic acid comprising a nucleotide sequence selected from the group consisting of:
   (a) a nucleotide sequence encoding an amino acid sequence comprising amino acids 49 to 684 of SEQ ID NO:2, and
   (b) a nucleotide sequence, the complete complement thereof which binds to said nucleotide sequence (a) under stringent hybridization conditions of a sodium concentration of 50–300 mM and a temperature of 42–68° C.,
   wherein said nucleic acid encodes a protein having glutaminase activity.

3. An isolated nucleic acid comprising a nucleotide sequence of SEQ ID NO:1, or a complete complement thereof which binds to SEQ ID NO:1 under stringent hybridization conditions of a sodium concentration of 50–300 mM and a temperature of 42–68° C.,
   wherein said nucleic acid encodes a protein having glutaminase activity.

4. A recombinant nucleic acid comprising the nucleotide sequence of claim 3.

5. A transformant or a transductant comprising the recombinant nucleic acid according to claim 4.

6. A process for producing a glutaminase which comprises culturing the transformant or the transductant according to claim 5 in a culture medium; and collecting glutaminase from said culture medium.

7. A recombinant nucleic acid comprising the nucleotide sequence according to claim 1.

8. A recombinant nucleic acid comprising the nucleotide sequence according to claim 2.

9. A transformant or a transductant comprising the recombinant nucleic acid according to claim 7.

10. A transformant or a transductant comprising the recombinant nucleic acid according to claim 8.

11. A process for producing glutaminase which comprises culturing the transformant or the transductant according to claim 9 and collecting glutaminase from a culture medium.

12. A process for producing glutaminase which comprises culturing the transformant or the transductant according to claim 10 and collecting glutaminase from a culture medium.

* * * * *